United States Patent [19]

Annis et al.

[11] Patent Number: 5,557,039

[45] Date of Patent: Sep. 17, 1996

[54] MATERIALS EVALUATOR

[75] Inventors: Patricia A. Annis, Athens; Ronald C. Davis, Watkinsville, both of Ga.; Randall R. Bresee, Knoxville, Tenn.

[73] Assignee: University of Georgia Research Foundation, Inc., Athens, Ga.

[21] Appl. No.: 252,754

[22] Filed: Jun. 2, 1994

[51] Int. Cl.$^6$ ................................... G01N 3/56
[52] U.S. Cl. ............................................. 73/7
[58] Field of Search ................................. 73/7

[56] References Cited

U.S. PATENT DOCUMENTS

| | | | |
|---|---|---|---|
| 2,100,332 | 11/1937 | Hathaway et al. | 73/7 |
| 2,251,681 | 8/1941 | Hathaway et al. | 73/7 |
| 2,584,156 | 2/1952 | Packer | 73/7 |
| 2,734,375 | 2/1956 | Galbraith et al. | 73/7 |
| 2,815,658 | 12/1957 | Press | 73/7 |
| 2,895,326 | 7/1959 | Fesperman et al. | 73/7 |
| 3,641,807 | 2/1972 | Brooks | 73/7 |
| 3,835,697 | 9/1974 | Schneider et al. | 73/7 |
| 3,961,521 | 6/1976 | Bailey et al. | 73/7 |
| 4,462,245 | 7/1984 | Gould et al. | 73/7 |
| 4,537,059 | 8/1985 | Sokolovsky | 73/7 |
| 4,864,852 | 9/1989 | Boone | 73/7 X |
| 4,936,135 | 6/1990 | Annis et al. | 73/7 |
| 5,343,733 | 9/1994 | Nakagawa et al. | 73/7 |

FOREIGN PATENT DOCUMENTS

| | | |
|---|---|---|
| 0378496 | 2/1923 | Germany . |
| 748178 | 7/1980 | U.S.S.R. . |
| 1146265 | 3/1969 | United Kingdom . |

OTHER PUBLICATIONS

Pal et al., "Friction and Wear Characteristics of Plastic Guides", J. Inst. Eng. Mech. Eng. Div., vol. 50, No. 11, Jul. 1970. pp. 298–306.

H. Bar–Yecheskel & A. Weinberg, "An Improved Testing Instrument for the Evaluation of the Shedding or Defuzzing of Fibres in Finished Garments," 79 J. Text Inst. No. 4, pp. 643–647 (1988).

J. Hearle & J. Amirbayat, "The Design of a Multipurpose Fabric Tester," 79 J. Text Inst., No. 4, pp. 588–597 (1988).

J. Amirbayat and W. D. Cooke, "Change in Surface Properties of Fabrics During Wear," 59 Textile Research Journal No. 8, pp. 469–477 (Aug. 1989).

Annis, P. A. and R. R. Bresee, "Comparing Actual Fabric Wear with Laboratory Abrasion and Laundering," Textile Chemist and Colorist, vol. 26, No. 1, Jan. 1994. pp. 17–23.

Annis, P. A., "Commercialization of the Annis–Bresee Materials Evaluator," submitted to the Advanced Technology Development Center, Atlanta, Georgia, Apr. 2, 1993. 19 pages.

(List continued on next page.)

*Primary Examiner*—Thomas P. Noland
*Attorney, Agent, or Firm*—James L. Ewing, IV; Mitchell G. Stockwell; Kilpatrick & Cody

[57] ABSTRACT

Devices and processes are disclosed for controlling and measuring precisely the many variables associated with fiber wear and transfer among materials. Specifically, one embodiment of the invention involves a slide and track arrangement for translating rotary motion of a crank shaft into reciprocal or, if desired, orbital motion of a second pad holding a sample or abrasive material against a first pad holding a sample material. The translation apparatus is such that even when orbital motion is selected, a constant angular relationship between the pattern of the materials held on the first pad and second pad is maintained. Devices are provided for controlling the speed of the motor; measuring the cyclical motion of the second pad; measuring and displaying the amount of load the second pad applies to the first pad and adjusting that load; changing and measuring the tension applied to the sample and/or abrasive materials and changing the angular orientation of the material on the first pad with respect to the material on the second pad. Thus, numerous variables that affect material wear are controlled or closely monitored, thereby allowing better understanding of the complexities of material wear.

18 Claims, 3 Drawing Sheets

OTHER PUBLICATIONS

ASTM Designation: D 4157–82, "Standard Test Method for Abrasion Resistance of Textile Fabrics (Oscillatory Cylinder Method)," ASTM Annual Book of Standards, Philadelphia, Pennsylvania, 1988, vol. 7.01. pp. 790–793.

ASTM Designation: D 4158–82. "Standard Test Method for Abrasion Resistance of Textile Fabrics (Uniform Abrasion Method)," ASTM Annual Book of Standards, Philadelphia, Pennsylvania, 1988, vol. 7.01. pp. 754–799.

ASTM Designation: D 3884–80, "Standard Test Method for Abrasion Resistance of Textile Fabrics (Rotary Platform, Double Head Method)," ASTM Annual Book of Standards, Philadelphia, Pennsylvania, 1988, vol. 7.01. pp. 643–647.

ASTM Designation: D 3885–80, "Standard Test Method for Abrasion Resistance of Textile Fabrics (Flexing and Abrasion Method)," ASTM Annual Book of Standards, Philadelphia, Pennsylvania, 1988, vol. 7.01. pp. 648–652.

ASTM Designation: D 3886–80, "Standard Test Method for Abrasion Resistance of Textile Fabrics (Inflated Diaphragm Method)," ASTM Annual Book of Standards, Philadelphia, Pennsylvania, 1988, vol. 7.01. pp. 653–656.

AATCC Test Method 93–1984, "Abrasion Resistance of Fabrics: Accelerotor Method," AATCC (American Association of Textile Chemists and Colorists) Technical Manual, Research Triangle Park, North Carolina, 1988, vol. 63. pp. 133–135.

ASTM Designation: D 3511–82, "Standard Test Method for Pilling Resistance and Other Related Surface Changes of Textile Fabrics Brush Pilling Tester Method," ASTM Annual Book of Standards, Philadelphia, Pennsylvania, 1988, vol. 7.01. pp. 526–529.

ASTM Designation: D 3512–82, "Standard Test Method for Pilling Resistance and Other Related Surface Changes of Textile Fabrics: Random Tumble Pilling Tester Method," ASTM Annual Book of Standards, Philadelphia, Pennsylvania, 1988, vol. 7.01. pp. 530–534.

Product Brochure Entitled "Atlas Random Tumble Pilling Tester," provided by Atlas Electric Devices Company, Oct–1987, (two pages).

Product Brochure Entitled "Abrasers," provided by Teledyne Taber, undated (twelve pages). but by Nov. 1994.

Product Brochure Entitled "The CSI Stoll–Quartermaster Universal Wear Tester," provided by Custom Scientific Instruments, Inc., a Division of Atlas Electric Devices Co., undated (four pages). but by Nov. 1994.

Product Brochure Entitled "Specialists in Environmental and Material Testing," provided by Atlas Devices Company, undated (six and one–half pages). but by Nov. 1994.

Product Brochure Entitled "TMI–New Capabilities for a New Era," provided by Testing Machines, Inc., 1985 (forty pages).

Product Brochure Entitled "CSI Customer Scientific Instruments, Inc.—Specialists in Physical Testing Instrumentation," provided by Customer Scienctific Instruments, Inc., 1985 (twenty pages).

Product Brochure Entitled "Martindale Pilling Conversion," published by James H. Heal & Co. Ltd. of England during Apr. of 1991 (one page).

Product Brochure Entitled "Nu–Martindale abrasion and pilling tester," published by James H. Heal & Co. Ltd. of England during Aug. of 1993 (four pages).

Product Brochure Entitled "Martindale wear and abrasion tester," published by James H. Heal & Co. Ltd. of England during Dec. 1990 (two pages).

"Operating Instruction Manual for Martindale Wear and Abrasion Tester Model 103 Serial Nos. 103–1386/2 Upwards Martindale–Jul. 1, 1988," published by James H. Heal & Co. Ltd. of England at an unspecified date (seventeen pages). but by Nov. 1994.

Pilling Tester Model CS–53 Custom Scientific Instruments, Inc. 1 page. ASTM Desisnation D 1375 E. I. Dupont Bulletin X–46 1 page published by Nov. 1994 (attached to reference AR sheet 3).

Excerpt from *Melliand Textilberichte,* page 950 (Dec. 1992) with one page English translation (–440).

Panhuber, H., et al., International Wool Textile Organisation Technical Committee, "An Instrument for the Assessment of Pilled Fabrics Using Image Analysis," Mar. 1994, Report No. 19; (13 pages).

Ramgulam, R. B., et al., "The Objective Assessment of Fabric Pilling Part I: Methodology," 84 *J. Text. Inst.,* 221–226, (No. 2 1993).

Amirbayat, J., et al., "The Objective of Fabric Pilling Part II: Experimental Work," 85 *J. Text. Inst.,* 397–401, (No. 3 1994).

MATERIALS EVALUATOR

This invention relates to devices and techniques for testing wear properties of materials such as fabrics, paper board and the like.

BACKGROUND OF THE INVENTION

As is disclosed in U.S. Pat. No. 4,936,135 issued to Annis, et al. (incorporated herein by this reference), a number of devices have been developed for testing wear properties of materials. Such devices typically subject a material such as cloth or paper board to abrasion, flexion, tensile stress or cyclical impact. Frequently, the intent is to load the material under test to failure. Other techniques involve non-destructive testing.

Various types of devices have been created to test for "abrasion resistance." Abrasion resistance is often defined in terms of the number of cycles of abrasion applied by a specified machine, using a specified technique to produce a specified degree or amount of abrasion. Resistance of materials to abrasion as measured on a testing machine in the laboratory is generally only one of several factors contributing to "wear performance" or "durability" as experienced in the actual use of the material, however. "Durability" is frequently defined as the ability to withstand deterioration or destruction in use, including the effects of abrasion. Abrasion resistance and durability are frequently related, but their relationship varies with different end uses. Different factors, therefore, may be necessary to calculate durability from specific abrasion resistance data. Although laboratory abrasion resistance tests may be reliable to compare relative end use performance of materials where the differences in abrasion resistance of the materials are large, such tests are frequently unreliable where such differences are not large. In general, abrasion resistance test findings are unreliable for prediction of actual wear life in specific end uses unless data exists showing the specific relationship between the abrasion resistance test results and actual wear in the intended end use.

Abrasion resistance is affected by many factors in fabrics, such as the mechanical properties and dimensions of the fibers, the structure and geometry of yarns forming the fabric, the structure and geometry of the fabrics, and the type, kind and amount of finishing treatment to the fibers, yarns or fabrics.

Conventional Material Wear Testers

One type of abrasion-resistance testing device comprises an oscillating cylinder above which are placed several material specimen holding arms. Each arm comprises tension clamps and a pressure pad for mounting a specimen. Vacuum pipes suspended over the cylinder help remove lint and dust particles. The specimens may be tested for a number of properties, including average number of cycles to rupture, breaking load of specimens abraded for specific number of cycles, and changes in visual appearance such as luster, color, napping and pilling.

A second type of abrasion resistance testing device is known as the Schiefer machine. A material specimen is mounted on a smaller, circular abrading surface which is caused to rotate by a shaft upon which the surface is mounted. A larger circular surface which contacts the specimen carries an abradant. The abradant surface is mounted on a shaft which is parallel to but not coaxial with the shaft supporting the specimen surface. The pressure between the specimen and abradant may be adjusted and a resettable counter indicates the number of rotations in a test. The material specimens tested on the machine may be examined visually, abraded to destruction or examined for thickness, weight, electrical capacitance, absorption of beta emission from a radioactive surface or other appropriate properties. The measured values may be plotted against the number of rotations of abrasion to prepare an abrasion curve and thus an abrasion index for each material specimen.

A third type of abrasion resistance testing device is known as the rotary platform, double head abraser (Taber Abraser). A test specimen is mounted on a removable flat circular specimen holder. A pair of pivoted arms carries two abrasive wheels. The platform rotates and the abrasive wheels abrade the test material. After a predetermined number of revolutions, the test material may be evaluated for loss in breaking load and loss in mass or occurrence of yarn breakdown as a result of abrasion.

Another device for testing abrasion resistance properties of materials is the Stoll Quartermaster Universal Wear Tester. The machine subjects a material specimen to unidirectional reciprocal folding and rubbing over a bar having specified characteristics, under predetermined conditions of pressure and tension. The specimen may be abraded until failure or evaluated for percentage loss in breaking load or changes in luster, color, napping, pilling and thickness. The Stoll Quartermaster Universal Wear Tester also may be used for the inflated diaphragm method of testing abrasion resistance. In that case, the specimen is held in a fixed position and supported by an inflated rubber diaphragm which is held under constant pressure. The specimen is abraded by rubbing either unidirectionally or multidirectionally against an abradant having specified surface characteristics. Typically, the specimen is abraded until all fibers in the center of the abrasion area are worn off so that a contact pin in the abradant plate contacts a pin in the diaphragm underlying the cloth, thus actuating an electrical relay and stopping the machine upon failure so that cycles may be counted. The specimen also may be visually evaluated for changes in luster, color or fabric structure.

Yet another device for testing abrasion resistance of fabrics is commonly known as the Accelerotor. Specimens of material are cut and placed in a generally cylindrical chamber containing an impeller. The impeller rotor forces the specimens to impinge on the walls and abradant liner of the chamber and contemporaneously subjects the specimens to high velocity impacts. The specimen is subjected to flexing, rubbing, shock, compression, stretching and other mechanical forces during the test. Abrasion is produced throughout the specimen by rubbing yarn against yarn, fiber against fiber, specimen surface against specimen surface and specimen surface against abradant. Evaluation is typically based on weight loss or tensile strength loss of the specimen.

Other devices specifically test for pilling resistance rather than general abrasion resistance. Pills are bunches or balls of tangled fibers which are held to the surface of a fabric by one or more fibers. Pilling resistance may be defined as resistance to the formation of pills on a fabric. The pilling of fabrics is affected by several factors, including fiber type or blend, fiber dimensions, yarn and fabric construction and finishing treatments. The pilling resistance of a fabric in actual use varies from one user to the next and general conditions of use. Accordingly, garments of the same fabric will show varying resistances to pilling and greater variation in wear than do corresponding fabric specimens subjected to controlled laboratory tests.

One device for testing for pilling resistance is known as a Brush Pilling Tester. This testing machine includes two rotating platforms; a first which operates on a 19 mm radius at 58 rpm and a second which operates on a 6.5 mm radius at 58 rpm. Nylon brushes may be mounted on brush holders attached to one of the rotating platforms. Fabric specimens are mounted on circular fabric specimen holders so as to contact brushes or the fabric placed on the rotating platform. The specimens are brushed for a predetermined amount of time or cycles. The abraded specimens may be evaluated visually for amount and uniformity of pilling, as well as other surface changes such as fuzzing.

Another device for testing pilling resistance is known as the Random Tumble Pilling Tester. A fabric specimen is placed in a cylindrical chamber lined with a mildly abrasive material such as cork. Impellers subject the specimen to a variety of abrasive forces and the specimen is evaluated subjectively for degree of pilling and fuzzing.

The above-referenced devices and methods demonstrate the conventional wisdom of subjecting fabrics and other material to a large number of cycles of abrasion or other abuse in order to determine when the material will fail or its wear characteristics and properties. Such methods are less appropriate, however, where one wishes to evaluate abrasion resistance before failure or fiber transfer mechanisms and their effects upon material wear and durability.

Mechanisms Of Fiber Transfer

Mechanical interactions are primarily responsible for the transfer of fibers from a fabric to another object during contact. Mechanisms of fiber transfer have been found to occur by the following three mechanisms: loose fiber exchange, fiber slippage, and direct fragmentation. Although any one of these transfer mechanisms could predominate under certain conditions, all three mechanisms could occur simultaneously during many contact situations.

Loose fiber exchange from a donor fabric to a recipient fabric occurs when "unattached fibers" are shed or exchanged during surface contact. Previous surface abrasion and normal wear or maintenance procedures may be responsible for the presence of loose fibers on a fabric surface. The physical nature of "unattached" or "loose" fibers has not been precisely defined but generally is thought to apply to fibers lacking the usual means for securing the fibers in textile structures, such as fiber entanglements and yarn interlacings. Loose fibers on the surface of a textile are responsible for the large number of fibers transferred during the initial contact of a new textile and the progressive decrease in the number of fibers transferred during consecutive contacts. Of course, any action during contact that produces more loose fibers on the fabric surface would be expected to modify this behavior. This decreasing number of transferred fibers is most likely to be observed at low pressure levels since high pressures are not required to remove loose fibers and may increase fiber entanglements, so fibers become entrapped rather than exist loosely on a fabric's surface. After most of the surface fibers are shed, a different mechanism must take over if additional transfer is to occur.

Fiber slippage, a second transfer mechanism, involves the removal of whole fibers from a textile structure. During abrasion, mechanical forces accompanying surface contact cause fibers to be pulled from the yarn by slipping past other fibers in the textile structure. Fibers transferred by this mechanism often are of identical length to those in the yarn. Transfer attributed to the slippage mechanism has been observed in experiments using smooth, tightly woven recipient fabrics. For example, relatively fewer fibers were transferred to a cotton laboratory coat than to coarse-textured jackets and sweaters in one experiment. Those fibers that did transfer to the laboratory coat were considerably longer in length than the fibers transferred to other fabrics. Thus, a smooth recipient surface apparently is less likely to promote transfer of loose fibers or short fiber fragments (even at high contact pressures or after a number of consecutive contact passes) than a rough recipient surface.

Fiber slippage of long fiber lengths has previously been considered to be a relatively minor transfer mechanism because most fibers observed after transfer are shorter than 5.0 mm in length, a length shorter than that of fibers usually found in yarns. However, evidence obtained from actual forensic science work indicates that fabrics comprised solely of continuous filament fibers apparently transfer fibers to a variety of objects. This observation suggests that the contribution of the slippage mechanism to fiber transfer may be that it accompanies direct fragmentation.

Direct fragmentation of textile fibers is the third important mechanism of fiber transfer. Increasing amounts of contact pressure would ordinarily be expected to increase fiber fragmentation. Experiments have shown that the number of fibers transferred from fabrics increases with an increase in contact pressure and, in one study, as many as 60% of the fibers transferred at high pressures were attributed to direct fragmentation. See, C. Pounds and K. Smalldon, "The Transfer of Fibres Between Clothing Materials During Simulated Contacts and Their Persistence During Wear," Parts I–III, 15 *Journal of the Forensic Science Society* 15–27, 29–37, 197–207 (1975), which is incorporated herein by this reference. It also was found in this study that 20% of all transferred fibers were produced by direct fragmentation after one contact pass, whereas 100% of the transferred fibers were fragmented after eight consecutive passes. These observations suggest that fragmentation may accompany other mechanisms in the transfer process.

The mechanism of fiber fragmentation also may account for the effect of pressure level and recipient fabric texture on the length of fibers transferred. That is, a higher proportion of short fibers are transferred at higher pressures than at lower pressures, and coarse-textured fabrics consistently accumulate more transferred fiber fragments than smooth-textured fabrics, especially at high pressures.

Fiber fragmentation probably plays a major role in fiber transfer. This proposition is supported by the fact that most transferred fibers range in length from 0.5–10 mm with the majority being less than 2.5 mm. The transfer of intact staple or continuous filament fibers several centimeters in length or longer is less commonly observed. Fracture may be responsible for the formation of surface fragments which later participate in loose fiber exchange or fiber slippage that occurs as a secondary event following fracture. Fiber fragments may be transferred directly or after the fragments have escaped entrapment from the yarn mass. On the other hand, the presence of fiber fragments also may be attributed to the natural distribution of fiber lengths which often include a substantial portion of very short lengths. To ascertain the role of fragmentation in fiber transfer, extensive measurements of fiber length distributions are necessary, especially after abrasive actions accompanying textile use.

The contribution of each of the three mechanisms mentioned above to fiber transfer depends on the nature of the donor and recipient fabrics involved in the surface contact, the pressure applied during contact, and the number of contact passes. However, explanations of transfer behavior in terms of textile structural characteristics have been meager, at best. Factors that affect such behavior include fiber length, denier and breaking force, yarn linear density, spinning system and twist, fabric construction, thread count, weight, thickness, specific volume, cover factor and float length.

Secondary Fiber Transfer and Fiber Redeposition

Secondary fiber transfer occurs when a fiber is transferred from its original source to a second object after initial transfer through an intermediate object. Secondary fiber transfer includes reverse transfer (back transfer), or environmental transfer. It occurs readily between textile materials and horizontal surfaces through the effect of gravity (environmental transfer) as well as between two textiles as in primary fiber transfer (reverse transfer).

The existence of secondary fiber transfer was first confirmed by Pounds and Smalldon, mentioned above, during surface contact experiments between wool donor fabrics and wool, acrylic, and wool-acrylic recipients. After two contact passes as many as 60% of the transferred fibers were redeposited back to the surface of the original donor fabric. As in primary fiber transfer, secondary fiber transfer appears to increase as the area of surface contact between the two fabrics increases. To minimize the effect of secondary fiber transfer during contact experiments, transferred fibers usually are removed from the recipient fabric after each successive contact pass. This procedure increases the apparent number of fibers transferred from a donor to a recipient garment because these fibers are retrieved and counted rather than redeposited onto the surface of the donor fabric.

Fiber redeposition, a type of secondary fiber transfer, is the release of a transferred fiber from the surface of a recipient fabric and relocation of that fiber to another point on the same recipient fabric. A wear study designed to determine the extent and nature of the redistribution of wool and nylon fibers from cotton and cotton-polyester fabrics found that as many as 38% of the original transferred fibers were relocated to other areas of clothing after approximately four hours of wear. See, J. Robertson and A. Lloyd, "Observations on Redistribution of Textile Fibres," 24 *Journal of the Forensic Science Society* No. 4, 3–7 (1984), which is incorporated herein by this reference. Only 1% of these fibers were found on the inner edges (waistbands and hems) of the experimental garments. Although few statistics were compiled, the redeposited fibers were equally likely to be found on the outer surface of dress weight fabrics as on the outer surface of bottom weight fabrics. In this study, the extent of fiber redistribution was found to depend on the nature of the recipient garment, length of wear, outer clothing worn, and activities during wear. Other studies show that the extent of fiber transfer/redeposition depends upon generic fiber type, length, and mass, yarn and fabric surface texture, degree of attachment between transferred fibers and recipient fabric, and degree of abrasion.

In the secondary fiber transfer process, fiber removal and fiber attachment must be considered simultaneously. Therefore, mechanisms of both fiber transfer and persistence could influence secondary fiber transfer either directly or through an interaction of both processes. Since secondary fiber transfer involves the rapid exchange of a considerable number of loose fibers, it is probable that these fibers are held on the surface of the recipient fabric in a loosely bound state. Fibers that are tightly bound would be less likely to participate in secondary transfer/redeposition. The removal of these transferred fibers during subsequent surface contact could then occur by any one of the three mechanisms of fiber transfer (loose fiber exchange, fiber slippage, or direct fragmentation) with the mechanism of loose fiber exchange predominating.

Experimental studies of secondary fiber transfer have demonstrated the importance of fiber length, generic class and mass and fabric texture and construction on the extent of secondary fiber transfer and redeposition during short periods of wear. Location, size of contact area, the number of contact passes, garment fit, the wearing of outer garments, activity during wear, and washing procedures also are significant.

Abrasion of Textile Materials

Fiber transfer occurs in response to mechanical stresses encountered during abrasive contact. An evaluation of the mechanisms of textile abrasion provides insight into relationships between structural characteristics of textiles and fiber transfer. A clearer understanding of the mechanisms governing fiber transfer also can be obtained.

Abrasion is the physical destruction of fibers, yarns, and fabrics resulting from the contact and relative motion of a textile surface with that of another surface. That is, abrasion is the wearing away of a material's surface. Abrasive damage to textiles during use can result from external abradants such as another textile or hard surfaces with rough or smooth textures. In addition, a fabric can abrade itself. Internal abrasion results from the flexing and bending of fibers and yarns over each other in fabrics. Abrasive damage to fabrics can result in degradation of mechanical and/or aesthetic properties.

The general mechanisms of textile abrasion are borrowed from the theories of contact physics. The theories of frictional attrition of solid metal bodies can be applied to fibrous assemblies if modifications are made to accommodate the viscoelastic properties of textile fibers and the complex structural geometry of fabrics. Three mechanisms that contribute to the abrasive degradation of textiles are direct frictional wear, surface cutting, and fiber plucking or snagging. Common to all three mechanisms is the development of stress and frictional forces within fibers and yarns which eventually lead to the breakdown of structure. The stresses that develop during abrasive contact include tension, shear, torsion, bending, and compression. These abrasive forces occur repeatedly during normal textile use and care, are usually small in magnitude, and may result from external abrasion or interfiber interactions.

Direct frictional wear occurs when an abradant surface is relatively smooth and fibers are abraded while being firmly held within the structure of the textile. On the other hand, surface cutting of fibers occurs when the projections on an abradant surface are not smooth but rather are sharp and small relative to the size of the fiber. Frictional wear and surface cutting cause localized damage to fibers at points of contact. Fiber plucking or snagging occurs when abradant projections are large relative to a fiber's diameter and the pressure of the abradant on a fabric is large. Plucking or snagging may result in fracture, fiber slippage, or vertical displacement of fibers within the yarn.

In addition to damage caused by direct removal of fiber fragments, abrasive forces can destroy textile structures indirectly. Indirect or internal wear occurs as external abrasive forces are transmitted along the length of abraded fibers.

A force transverse to a yarn can result in displacement of fibers. These complex stress patterns can lead to fiber dislocation, cracking during bending, and/or transverse fracture if the interfiber frictional forces within the textile are relatively small. This breakdown of a textile structure may occur without appreciable fiber damage. If interfiber cohesive forces within a textile are large, bending and tensile stress can produce dynamic fatigue of individual fibers. If frictional forces are sufficiently large, fiber fracture will occur on the first contact. These internal mechanisms of abrasion may be considered the primary cause of textile abrasion in some cases. Fabrics and yarns are most resistant to the frictional forces of abrasion if interfiber cohesion is intermediate in magnitude.

Extensive research has been devoted to examining relationships between structural geometry and abrasion resistance of textile materials. Two factors are responsible for the abrasion resistance of textile structures: 1) the inherent abrasion resistance of the fibers and 2) the geometry of fiber arrangement. Fibers influence abrasion resistance by their response to mechanical stress, their effects on interfiber cohesion within yarns, and their ability to absorb and transmit abrasive stress during wear. Fiber structural parameters that influence abrasion resistance include length, linear density, three dimensional configuration (crimp), internal morphology, cross sectional shape, and surface texture. Mechanical properties of fibers that influence their abrasion resistance include tensile strength, shear strength, bending strength, compressional resiliency, torsional strength, elongation, creep and elastic recovery.

Geometric factors are known to influence the area of contact between a fabric and an abradant, the energy absorption capability of fabrics, and the relative movement of fibers and yarns within textile structures. Such geometric factors of yarns responsible for the abrasion resistance of textile materials are the relevant spinning system, linear density, twist (magnitude and direction), ply and surface texture. Other factors for fabrics are construction type, area density, thread count, float length, thickness and cover.

Single fiber transfer probably is influenced by both external and internal frictional forces. Investigations of fiber transfer during abrasive surface contact indicate transfer occurs as a result of direct fragmentation of fibers, loose fiber loss, and fiber slippage. External frictional forces (direct frictional wear and surface cutting) could be responsible for fragmentation and loose fiber transfer mechanisms. The formation of short fiber fragments could occur during abrasive surface contact or prior to the contact event (due to previous wear). Direct fragmentation is believed to predominate at high contact pressures and with coarse textured abradants (i.e., surface projections are large relative to the fiber diameter). Loose fiber ends or fiber fragments may act to deform and weaken other surface fibers and eventually produce fatigue. One study of the morphological changes in wool fibers during wear and abrasion testing found that the thinning of woven wool fabrics was due to the production and loss of short fiber fragments with fiber damage occurring primarily in the cross-over regions of the warp and filling yarns. See, C. Anderson and V. Robinson, "Morphological Changes in Wool Fibers During Fabric Wear and Abrasion Testing," 62 *Journal of the Textile Institute* No. 10, 281–86 (1971), (incorporated herein by this reference). On the other hand, fiber damage was not localized in knitted fabrics and occurred randomly throughout the fabric structure. The type of damage sustained by the wool fibers depended upon rate, degree, and location of the abrasive wear. Processes such as bleaching, mercerization, resin finishing and laundering also affected direct fragmentation and surface cutting.

The transfer mechanism of fiber slippage probably is related to external frictional forces (plucking) and/or to internal abrasion of fibers in the yarns of a fabric. Both mechanical processes could result in the removal of single fibers from textile structures. Fiber removal by the slippage mechanism occurs readily at low contact pressures. Loosely woven fabrics, fabrics with relatively long floats, and loosely twisted yarns are known to be more susceptible to fiber slippage than tightly woven fabrics having shorter yarn cross-over lengths and tightly twisted yarns. Frictional forces also may contribute to the degradation of synthetic double knits by snagging and pilling. These fabrics frequently are composed of high strength continuous filament yarns having low interfiber cohesion and high mobility.

Pilling of Textiles

Pills are bundles of entangled fibers which are formed on the surface of fabrics during abrasion. Examining textile structural characteristics associated with pilling may contribute to the understanding of fiber transfer, since fiber transfer and pilling both involve complex fiber interactions and subsequent displacement of single fibers from their original position in textile structures. Fiber transfer is related to pilling in another important way, as well. Both phenomena are wear-related properties induced by mechanical action. Hence, the mechanical mechanisms responsible for pilling probably also govern fiber transfer. Furthermore, the same fiber, yarn, and fabric structural parameters that influence pilling probably also influence fiber transfer.

The process of pilling is believed to proceed through four main stages: fuzz formation, fiber entanglement, pill growth, and pill wear-off. Fuzz formation is initiated by the brushing up of free fiber ends not secured within the textile structure and conversion of loose fiber loops into free fiber ends. To bring a free fiber end to the fabric surface, it is necessary to slide, bend, and twist the fiber around its neighbors against the forces of friction which tend to hold fibers in place. A similar mechanism can be envisioned during fiber transfer. The fracture of fibers may occur in situations where frictional forces exceed the fiber's breaking strength. Fiber slippage may occur in situations where interfiber frictional forces are overcome. Loose fibers, formed by fracture or slippage, may subsequently participate in fiber transfer. It has been conjectured that loose fibers generally do not participate in pill formation but rather drop off continuously throughout the abrasion process accompanying pill formation. Pounds and Smalldon in the articles mentioned above also observed the slippage and loss of fiber fragments during contact experiments between knitted donor fabrics and coarse textured recipient fabrics. The mean fiber length of these transferred fibers was considerably longer at low contact pressures than at high contact pressures. These results indicate that fracture is favored at higher contact pressures. The propensity for fuzz formation can be attributed to the length, linear density, flexural rigidity, and abrasion resistance of individual fibers. These properties, in turn, influence the frictional and tensile properties of textile fibers. Hence, fiber slippage and/or fracture associated with transfer also may be influenced by these fiber mechanical properties.

Fiber entanglements in pills result when free fuzz fibers or foreign fibers roll and subsequently snarl with fibers secured in the textile. Entangled fibers on the fabric surface are more susceptible to abrasive forces than unentangled fibers and may suffer fatigue and/or fracture. This abrasive damage is seen as transverse cracking caused by biaxial-type fatigue that occurs discontinuously along the length of the fiber. It has been suggested that some of these entangled fibers fracture and are lost from fabric surfaces during wear. W. Cooke, "The Influence of Fibre Fatigue on the Pilling Cycle," Parts I–III, 73–75 *Journal of the Textile Institute* (1982–84), (incorporated herein by this reference). Entangled fibers and the subsequent production of loose and/or fractured fibers during abrasive surface contact probably is one explanation for the presence of fibers that are later transferred via slippage and exchange mechanisms. The propensity of fibers to entangle is affected by fiber linear density, flexural rigidity, crimp, and cross-sectional shape. These properties influence the elastic and tensile properties of textile fibers. It seems likely that fiber transfer also would be influenced by these structural parameters, although no direct evidence supporting this proposition is available.

After fiber entanglement, pill growth progresses as the density of fiber entanglements increase and a spherical mass is formed. During this process, anchor fibers may be pulled out of the textile structure and drawn up into the pill or fractured and lost. Alternatively, anchor fatigue may occur either close to the textile surface where fibers are securely held or at places along the anchor fiber where they are forced to bend around other fibers and suffer considerable stress as a result of these torsional and bending forces. These anchor fibers soon are lost from the fabric surface and contribute to the worn-off surface fuzz.

These mechanisms, or similar ones, probably also influence single fiber transfer. Anchor fracture during the pull-out/roll-up sequence could result in the formation of fiber fragments that are free to participate in fiber transfer. Furthermore, as long as pills do not become too tightly tangled, some fibers could become free and available for transfer. Fiber structural characteristics believed to be responsible for pill growth include flexural rigidity, cross-sectional shape, linear density, and elongation. These properties are known to influence the mechanical properties of textile fibers.

The last stage of pilling—pill wear-off—is believed to proceed by two different mechanisms. These are tensile break-off and pull-out and both involve the fatigue of anchor fibers. Tensile break-off occurs when the frictional load applied to a pill exceeds the combined tensile resistance of the anchor fibers. The anchor fibers fracture, and the pill is released. Pull-out occurs when the frictional load applied to a pill is less than the combined tensile resistance of the anchors but greater than the combined anchor frictional forces. In this case, anchor fibers slip and the pill is released.

It is possible that the mechanisms of break-off and pull-out function independently. However, it is more likely that both of these occur simultaneously and/or in combination with each other. In any event, pills either will be swept from fabric surfaces or disentangled and the loss of individual fibers observed. Pill wear-off is most likely to occur during wearing and laundering.

Mechanisms similar to tensile break-off and pull-out could be a source of some of the loose fiber debris that participates in fiber transfer during fabric-to-fabric contact. In addition, the rate of fiber removal from a fabric surface during wear also may be influenced by wear-off mechanisms. Fiber parameters that influence pill wear-off include linear density, length, flexural rigidity, and abrasion resistance. These properties influence the tensile properties of textile fibers and the propensity for fracture and slippage.

Fiber structural characteristics believed to influence each stage of the pilling cycle are summarized as follows:

1. Fuzz Formation. Fiber length, linear density, three dimensional configuration (crimp), tensile strength, torsional strength, bending strength, interfiber transfer, interfiber friction, abrasion resistance.

2. Fuzz Entanglement. Fiber linear density, three dimensional configuration (crimp), cross-sectional shape, tensile strength, bending strength, elongation, elastic recovery, interfiber cohesion.

3. Pill Growth. Fiber length, linear density, cross-sectional shape, tensile strength, bending strength, torsional strength, elongation, electrostatic potential, crystallinity and polymer orientation.

4. Pill Wear-Off. Fiber length, linear density, generic class, tensile strength, bending strength, abrasion resistance, elongation.

In addition to the fiber properties discussed above, yarn structure, fabric construction, and finishing also can influence pilling of textile materials. For instance, fuzz formation can be reduced by manipulating yarn twist and hairiness. Fiber entanglement and pill growth can be controlled by careful selection of yarns, fabric, and finishing procedures that eliminate fiber movement within the yarn structure. Elimination of fiber slippage and fatigue prevents the pull-out/roll-up sequence described by Cooke in the articles mentioned above. Progressive transverse fatigue and eventual pill wear-off also are dependent on yarn and fabric properties. Yarn, fabric, and finish characteristics most likely to influence pilling in woven and knitted fabrics are summarized below:

1. Yarn. Linear density, uniformity, hairiness, ply, twist, interfiber cohesion, blend composition, spinning system.

2. Fabric. Fiber content, surface texture, thread count, area density, construction, fiber blend effects, cover.

3. Finish. Brushing, singeing, shearing, heat setting, lubricants, adhesives, resin treatments (wash and wear, durable press, and shrink resistant).

Some of the characteristics that influence pilling also could influence fiber transfer since the number of fibers transferred during contact probably is dependent on the nature of the fabrics involved. Researchers have observed that the number and length distribution of fibers transferred is influenced by the texture of recipient garments, with fewer fibers transferred to smooth textured garments than to coarse textured garments. However, another study found that the length distribution of transferred fibers was not significantly affected by the nature of either the donor or the recipient garment. Despite the discrepancies between these studies, fiber transfer appears to be influenced, at least to some degree, by fabric texture.

Investigations into the structure-property relationships of textile materials have shown that fiber, yarn, and fabric properties interact in complex ways during pilling. Various mathematical models have been proposed that correlate key structural parameters with the mechanistic steps of the pilling process. These models resemble flow diagrams that represent each stage in the pilling process. The transition from one stage to another is dependent on the previous stage and the rate is specific for a particular fiber-fabric combination.

The usefulness of any model that depicts pilling is determined by: 1) its ability to explain the physical changes that occur during real pilling and 2) whether it can be used to predict the pilling behavior of fabrics with new or postulated properties. One model contains the minimum number of parameters for evaluating the basic phenomenon of pilling. See, W. Conti and E. Tassinari, "Simplified Kinetic Model for the Mechanism of Pilling," 65 *Journal of the Textile Institute* No. 3, 267–73 (1974) (incorporated herein by this reference). The parameters in this model are obtained directly from analysis of the results of any standardized pill-testing method. The rate of fuzz entanglement to form pills and the rate of pill disappearance through disentanglement affect the relationship between pillable fuzz and the number of pills, while rate of pill wear off affects the relationship between the number of pills and worn off pills. Another model, proposed by Cooke and Arthur is considerably more complex but more accurately represents pilling of fabrics made from staple fiber yarns. See, W. Cooke and D. Arthur, "A Simulation Model of the Pilling Process," 72 *Journal of the Textile Institute* No. 3, 111–20 (1981), (incorporated herein by this reference). The parameters in this model are obtained directly from experimental measurements of fibers, yarns, and fabrics. That model posits that abrasion of loop fuzz and fiber ends results in the formation of non-pillable fuzz, pillable fuzz, non-pillable loops and/or pillable loops. Non-pillable fuzz subsequently can form worn off fuzz, while pillable fuzz forms either pills or worn off fuzz. Untangled pills can, in reverse, form pillable fuzz or they can become worn off pills or worn off fuzz. By the same token, worn off pills can once again form pills. Non-pillable loops can cause non-pillable fuzz, pillable fuzz or pillable loops. Pillable loops also could eventually become pillable fuzz or reform into pills.

Mathematical models of pilling could serve as a basis for the development of models depicting the fiber transfer process. Such models would trace the history of transferred fibers as they are removed from the yarn bundle, redeposited during fabric-to-fabric contact, and, subsequently, lost from or retained on a fabric's surface. Model parameters would be measured experimentally from simulated wear tests on fiber, yarns, and fabrics. A model depicting fiber transfer would aid in understanding the functional relationships between fiber, yarn, and fabric structural parameters and the mechanisms of fiber transfer. Furthermore, a model of fiber transfer would be a useful tool for predicting the general behavior of fabrics when subjected to surface abrasion and wear.

Snagging of Textiles

Another property affecting textile wear is snagging. Snags are fabric defects caused by (or due to) the pulling or plucking of yarn(s) or filaments from a fabric surface. Knitted fabrics are more susceptible to snagging than woven fabrics because of their loose loop construction. Because snagging is a wear related property, the structural characteristics that influence snagging also could influence fiber transfer.

Snagging is believed to proceed through two main stages: initiation and propagation. Snag initiation occurs during biaxial deformation when an asperity or the rough surface of an object plucks a yarn or a portion of a yarn from the fabric surface. Snagging is most likely to occur along the loop sides of the three-dimensional knit stitch. Propagation of the snag occurs as the plucked loop is distended or as it catches and breaks. Loose fibers exposed after snag fracture could participate in fiber transfer. Furthermore, snag initiation and propagation are governed by the accessibility of the fibers and yarns in a particular knit structure as is fiber transfer.

Important structural characteristics that influence snagging include stitch tightness, yarn twist, fabric density, and the accessibility of fibers and yarns in the knit structure. Characteristics that influence fiber/yarn accessibility include fiber length, denier, crimp and blend levels, yarn spinning system, diameter and ply, and stitch structure, loop configuration, wale spacing, and float length. These properties influence frictional coefficients (cohesiveness), bending rigidity, and tensile strength of fibers, yarns, and fabrics. One would expect the process and mechanisms of fiber transfer to be influenced by these mechanical properties also. Snags on worn fabric surfaces may be an important source of transferred fibers and the frictional and mechanical properties that influence snagging also would be expected to influence single fiber transfer.

Influence of Structural Characteristics on Mechanical Properties

Theoretically, any fiber, yarn, fabric, or finish characteristic that influences fiber mobility could influence single fiber transfer. Investigations concerning the influence of fiber, yarn, fabric, or finish parameters on mechanical properties of textiles vary in scope and intent. Early studies examined the wear resistance of garments subjected to stress during production and use. Other research was devoted to developing instrumentation and testing procedures which simulated wear in an attempt to correlate data observed in the laboratory with actual textile use. Various theories and models have been proposed which allow quantitative analysis and prediction of the behavior of different fibers and fabrics during abrasion, pilling, and wear. The mechanical properties of textiles are influenced by a complex interaction among fiber, yarn, fabric, and finish parameters.

Fiber Properties

Fiber characteristics influence mechanical wear performance by affecting interfiber cohesion and absorption of work or energy. Fiber diameter is generally considered one of the most important fiber characteristics affecting textile performance during wear. Increasing fiber diameter generally increases yarn abrasion resistance and decreases hairiness. In addition, an increase in fiber diameter causes a proportional decrease in yarn tensile strength and extension due to increases in naps and irregularities and a decrease in interfiber cohesion. Increasing fiber diameter also improves the abrasion resistance of woven and knitted fabrics, reduces fabric pilling by reducing fuzz formation, and pill growth, increases stiffness and reduces tensile strength, fabric extension, knitted fabric bursting strength, and snagging propensity.

Fiber length is regarded as being the second most important factor affecting wear performance of textile materials. Increasing mean fiber length generally improves yarn tensile properties, increases yarn abrasion resistance and reduces yarn hairiness. Variation in staple length increases the lint-shedding tendencies of cotton knitting yarns due to a large proportion of protruding fiber ends and the tendency for shorter fibers to migrate to the yarn surface during yarn manufacture. Although the effect of fiber length is less for fabrics than for yarns due to yarn interlacing, increasing mean fiber length improves the abrasion resistance of woven and knitted fabrics, reduces pilling propensity by preventing fuzz formation, pill growth and pill wear-off, reduces yarn hairiness, and increases tensile and bursting strength of woven and knitted fabrics.

Yarn Structure

Properties of yarns depend on properties of the constituent fibers and the arrangement of fibers in the yarns. Yarn structural features that influence mechanical wear properties are those that affect their ability to absorb abrasive stress repeatedly without failure or rupture. The relationship between wear properties and yarn diameter is well documented, with an increase in yarn diameter accompanied by improvements in flat and flex abrasion resistance. The abrasion resistance of satin and warp-faced twills can be significantly improved if larger yarns are used. Thicker yarns allow for a better distribution of stress; a larger number of fibers must be ruptured or displaced before yarn failure occurs. Increasing yarn diameter also generally decreases hairiness, lint shedding and pilling.

The relationship between yarn diameter and hairiness also could be important in fiber transfer. In one study on the abrasion characteristics of sewing threads differing in size and construction, it was reported that abrasion of coarse yarns resulted in the formation of large numbers of bruised and broken surface fibers, whereas surface damage was less discernible in the case of fine yarns, although a large number of plucked and/or pulled fibers tended to cluster into groups along the fine yarn. Consequently, the transfer mechanisms of direct fragmentation, fiber slippage, and loose surface fiber exchange could be a function of yarn diameter.

Yarn twist is another structural factor that influences textile durability during wear. Increasing twist generally improves abrasion resistance, although twist beyond an optimum level reduces yarn mobility and decreases abrasion resistance and strength because the capacity of yarns to flatten, rotate, and support transverse loads is reduced. Generally, the optimum twist level for staple yarns is greater than that for continuous filament yarns. Increasing yarn twist generally decreases pilling, yarn hairiness, and lint-shedding because fiber slippage is decreased. Yarn crimp and ply also affect wear properties of textiles because they influence contact area between a fabric surface and an abradant.

Yarn spinning systems influence the wear performance of textiles by controlling many yarn structural factors such as fiber orientation, entanglement, and mobility. Traditionally, ring spinning systems have been used to produce staple fiber yarns. The structure of ring spun yarns is characterized by internal homogeneity and a uniform twist distribution. Fibers in ring spun yarns are loosely bound and, therefore, highly mobile. Ring spun yarns have a hairy outer surface due to the protrusion of many fiber ends.

The structure of open-end rotor spun (OE) yarns differs considerably from that of ring spun yarns. Open-end yarns consist of a three-part structure. Fibers in the yarn interior are densely packed into a core of fibers that are aligned parallel with the yarn axis. In this respect, OE yarns resemble ring spun yarns. The middle portion of OE yarns is composed of loosely packed fibers twisted around the core and aligned on an angle to the axis. This intermediate zone extends up to the solid boundary of the yarn, and fibers in this area display less migration through the yarn interior due to differential twist levels caused by slippage inside the rotor. The outer portion of an OE yarn contains fibers that are wrapped around the yarn. Wrapper fibers are not completely secured inside the yarn interior but have a free end that is either helically wound along the yarn length or tightly wound in a localized manner perpendicular to the yarn axis. The frequency and characteristics of the wrapper fibers depends on spinning conditions and the properties of the fibers being spun. Wrapper fibers and other staple fiber ends protrude from the yarn surface and give OE yarns a hairy surface. Overall, differential twist levels and restricted fiber migration in OE spun yarns result in fibers that are less mobile and more rigidly bound than fibers in ring spun yarns. The mechanical properties of OE spun yarns are attributed largely to the structural components within the yarn. For example, yarn strength is strongly correlated with the proportion of axially aligned fibers in the yarn, whereas wrapper fibers are largely responsible for abrasion, pilling, and hairiness.

Air-jet spinning utilizes a high pressure vortex of air to twist fibers into a yarn. Air-jet spun yarns originally were considered a type of open-end yarn, although recent work suggests that air-jet spinning is a kind of false twist and wrapping system. Air-jet spun yarns are composed of a central core surrounded by wrapper fibers, but no distinct boundary separates these two zones. The core of air-jet spun yarns resembles the structure of a continuous filament false twisted yarn. The wrapper fibers are leading or trailing fiber ends that protrude from the core and either twist around the yarn core or migrate back into it. Most wrappers tend to lay on the yarn surface and resemble an irregular circular helix. Leading fiber ends may represent up to 85% of the wrapper fibers in the yarn bundle.

The appearance, structure, strength, and wear properties of air-jet spun yarns are determined by the number and twist of the wrapper fibers. Evenly spaced wrappers produce a yarn that resembles a ring spun yarn, whereas the presence of a large number of wrappers that are either loosely or tightly twisted produces yarns resembling OE or two-ply ring spun yarns, respectively. Generally, fibers in air-jet yarns are highly mobile due to lower levels of entanglement and twist.

Multifilament yarns are composed of twisted continuous filament fibers and are characterized by relatively few fiber entanglements and high level of lateral fiber mobility. Continuous filament yarns generally are stronger than staple fiber yarns because most of the fibers are arranged parallel to the yarn axis and are equally strained upon tensile loading. However, when continuous filament yarns are subjected to bending or compressional deformation, the cross-sectional shape of these yarns flattens. Collapse of the filament bundle increases the yarn surface-to-volume ratio and permits greater areas of contact with abradant surfaces that could result in filament fracture and increase susceptibility to pilling, snagging, and fiber transfer. However, sufficient twist, bulk-texturing techniques, and the development of stretch can produce continuous filament yarns that resist lateral deformation and are, therefore, stronger as well as more abrasion, pill, and snag resistant. In addition, continuous filament yarns are smooth and regular with few protruding fiber ends. They resist lint-shedding and are considerably less hairy than staple fiber yarns.

Yarns produced by different spinning systems vary in structural parameters that are known to influence the wear properties of textiles. Many yarn parameters, such as twist, hairiness, extensibility, and fiber mobility also may influence the transfer of single fibers. For instance, variations in twist, low levels of interfiber cohesion, and low levels of fiber migration characteristic of OE spun yarns may result in fiber shedding and subsequent transfer. In contrast, fiber transfer from loosely twisted, ring spun yarns might be expected to occur via the slippage mechanism. Open-end spun yarns are less hairy than conventional yarns with a predominance of short rather than long protruding fiber ends. Very short fiber protrusions would be less likely to fracture or slip during abrasive surface contact. The regularity, absence of naps, and lack of hairiness of OE yarns results in a smooth fabric surface. Fabrics with coarser surface textures are known to display more fiber transfer than fabrics with smooth surface textures.

When the fiber transfer properties of staple and continuous filament yarns are compared, one would expect the continuous filament yarns to transfer fewer fibers than staple length yarns due to the initial absence of short fiber lengths. However, the high levels of fiber mobility within these yarns would favor transfer by slippage should continuous filament fibers become fractured during use and care.

Based on the above discussion, yarn type may influence the nature and extent of single fiber transfer. Specifically, the relevant yarn spinning system (ring, OE and continuous filament), yarn linear density (count), and twist on the transfer properties of woven and knitted fabrics appear to affect fiber transfer.

An understanding of the transfer characteristics of fabrics produced from different yarn types is applicable to forensic science. The use of OE and air-jet spun yarns is increasing in apparel, household, and industrial textiles, especially in bottom weight fabrics (i.e., denims, workwear, automobile upholstery). These fabrics frequently are encountered during criminal investigations. Information on the transfer characteristics of these fabrics may enable forensic scientists to more accurately estimate the probability of chance match occurrences of fibers from these garment types.

Fabric Characteristics

Factors that influence the mechanical wear performance properties of textile materials affect the response of constituent fibers and yarns to mechanical stress. Increasing the number and ratio of yarn interlacings (thread count and balance, respectively) and decreasing interlacing length (float length) generally increases the abrasion resistance and strength of woven fabrics. Conversely, longer float lengths in basket, twill, and satin weaves, as opposed to short floats in plain weaves, usually result in a flexible fabric structure that is susceptible to snagging, slippage, and pilling. Fiber accessibility is greater in flexible, more loosely constructed fabrics. In addition, the surface texture of woven fabrics influences pilling, hairiness, and lint shedding by influencing the availability and accumulation of surface fibers.

Knitted fabrics are more loosely constructed than woven fabrics and are more flexible and less dimensionally stable during wear-related stress. Fiber accessibility and yarn mobility in knit fabrics are influenced by the number and type of interlacements and stitch length. Increasing stitch length generally increases snagging, pilling, and other abrasion damage due to decreasing interfiber and interyarn cohesion. The greater fabric specific volumes and lower cover factors found in knit fabrics could result in greater fiber accessibility compared to woven fabrics. Thus, knit fabrics would be expected to transfer more longer fibers by the slippage mechanism than woven fabrics.

Fiber transfer probably is influenced by a combination of these fabric construction parameters. Studies of fiber transfer with fabrics from a variety of new and worn garments that differ considerably in fiber content, yarn structure, and fabric characteristics indicate construction type, thread count, and texture may be especially significant.

The main objective of blending fibers is to produce yarns and fabrics with performance properties that are unobtainable using only one type of fiber. Fiber, yarn, and fabric structural characteristics and the interaction of these influence the wear properties of blended textiles. Tensile properties of blended yarns can be improved if linear density, length, and elongation of the different fiber components are similar. Of special importance to the properties of blended yarns and fabrics is the compatibility and homogeneity of the blended components. A uniform distribution of fibers along the yarn axis and throughout the cross-section generally optimizes the mechanical properties of yarns and fabrics. When fibers of different lengths and linear density are blended, the long and/or fine fibers often migrate to the yarn core whereas the short and/or coarse fibers migrate towards the yarn surface. In this situation, textiles no longer display the surface characteristics expected of an average blend. This phenomenon is especially important when surface properties such as fiber transfer are considered.

It has been reported that tensile strength is the most important mechanical property affected by fiber blending. S. Vinzanekar, D. Ajgaonkar, M. Talukdor and K. Kothawala, "Realization of Fibre Properties into Blended Yarns and Fabrics," *Blended Textiles*, Papers of the 38th All India Textile Conference, 94–109 (M. Gulrajani, ed. Nov. 18–20, 1981) (Textile Association of India, Bombay) (incorporated herein by this reference). Generally, yarn and fabric breaking strengths are improved by blending with long, fine fibers. Abrasion resistance of polyester-cotton fabrics may improve with increases in polyester content or deteriorate due to reductions in overall fiber extensibility and an inability to equally distribute loads. Blends containing relatively strong synthetic fibers that act as tenacious anchors promote fiber entanglement and prevent pill loss during wear. Blended yarns generally are also more hairy and prone to lint-shedding than yarns composed of one fiber type of a consistent length due to broadening of the fiber length distribution.

Understanding of the general principles underlying fiber transfer can be obtained from studies of carpet wear. During typical use, carpets are subjected to a variety of forces that include compression, shearing, and torsion. Laboratory and wear studies of carpet abrasion have shown that a loss in pile density is due to the formation and subsequent transfer of short fiber lengths. Other investigations of abrasive damage to individual carpet fibers using scanning electron microscopy suggest that the formation of fiber fragments is attributed to direct fragmentation that results from biaxial rotation, fibrillation, and transverse cracking, depending on fiber content of the carpet and nature of the abrasion. Fracture of carpet fibers was shown to occur near the tops of the tufts at the carpet surface and at bends or points of interfiber contact. Researchers also found that abraded carpet fibers were weakened at several places along their length before they broke at the most weakened location. These observations are consistent with results from preliminary studies of fiber transfer mechanisms in which multiple fracture of single fibers are hypothesized.

One study that compared fiber transfer characteristics of new and worn carpets found that fiber content was the most significant factor influencing the transfer of carpet fibers to footwear. See, J. Robertson and X. de Gamboa, "The Transfer of Carpet Fibres to Footwear," 10*th Triennial Conference of the International Association of Forensic Sciences*, Oxford, England (September 1984), (incorporated herein by this reference). The influence of the number of contact passes and carpet construction type on fiber transfer was less important. The authors of this study hypothesized that differences in transfer characteristics among new and worn carpets probably would decrease considerably after four to eight weeks as the new carpets became more compact and less prone to shedding. This theory was confirmed in another study which evaluated the transfer characteristics of new and used automobile carpeting. See, H. Scott, "The Persistence of Fibres Transferred During Contact of Automobile Carpets and Clothing Fibres," 18 *Journal of the Canadian Society of Forensic Science* No. 4, 185–99 (1985) (incorporated herein by this reference). The carpeting in late model vehicles transferred considerably more fibers than the carpeting in older vehicles. These results were attributed to natural wear and vacuuming, although quality and location of the carpeting and interactions between fibers of different generic type also may have influenced transfer.

Textile Finishes

Finishes are applied to textiles to modify appearance, hand, or performance. Such modifications may produce changes in mechanical properties, including pilling and other types of abrasion resistance. The nature and extent of fiber transfer probably is influenced to some degree by textile finishing procedures. Finishes generally are classified as mechanical, chemical, or additive.

Mechanical finishes physically alter the structure of textiles. Woven and knitted fabrics are routinely brushed, singed, and sheared to reduce pilling. These techniques are considered to be the primary method of reducing pilling propensity of woven fabrics composed of 100% polyester or polyester-cotton blends. Brushing, followed by shearing, is reported to be especially effective in reducing the pilling of tightly constructed fabrics. These mechanical finishing methods probably prevent pilling because loose fiber ends that could be involved in fuzz formation and fiber entanglement are lifted up and removed greatly shortened.

Chemical finishes modify the chemical structure of textile fibers and have the effect of often modifying fiber mechanical properties. For example, chemical finishing agents which impart crease and shrink resistance, water repellency, and flame retardancy are known to influence the abrasion resistance of textile materials. After abrasion crosslinked cotton fabrics are less likely to develop a fuzzy surface than untreated fabrics. This behavior could significantly influence a fabric's propensity for fiber transfer. Resin treated fabrics which have been desized, scoured, bleached and mercerized were found to develop fewer broken fiber ends after surface abrasion than similar untreated fabrics which had been subjected to similar finishing procedures but no resin treatment. Scanning electron photomicrographs of unabraded and abraded fabrics also have shown that resin treatments decrease surface hairiness and increase yarn thinning. The application of cross-linking agents can be accompanied by losses in fabric strength and suppleness. Apparently, chemical crosslinking reduces fiber and fabric elongation which prevents fibers from twisting and rolling during abrasion. The potential for absorption of energy is, thereby, reduced and fiber fracture occurs. After fracture, additional abrasive forces gradually shorten the remaining fiber ends which fall out of the fabric structure.

Pilling and tensile properties have been shown to be influenced by chemical finishes. Mercerization results in fiber swelling and a corresponding reduction in overall fabric dimension which results in an increase in interfiber cohesion, prevention of fuzz formation and fiber entanglement, and reduction of fiber slippage during abrasion. Increases in anchor fatigue and pill wear-off rates also can be attributed to decreases in fiber strength and extensibility. In addition, chemical finishes that reduce fiber elasticity could influence fiber transfer either by preventing fiber slippage or by promoting direct fragmentation and subsequent fiber loss.

Additive finishes are substances that are deposited on textile surfaces to improve fabric hand, appearance, soil resistance, wrinkle resistance, and water repellency. Additive finishes also modify mechanical properties of textiles by influencing fiber and yarn mobility. Bindings and coatings which are deposited on the surface of a textile in the form of discrete particles or as films improve resistance to flat abrasion because the additives absorb some of the applied mechanical energy. It has been observed, for instance, that polymer coatings improve flat abrasion resistance and pilling resistance, increase breaking strength, and reduce fuzz formation on cotton fabrics. The stiffening effects of some additive finishes could reduce flex and edge abrasion resistance because increases in interfiber cohesion reduce fiber and yarn mobility. On the other hand, lubricants and softeners increase fiber and yarn mobility by encasing fibers in smooth films. The surface characteristics of textiles can be altered considerably by changes in fiber mobility. It has been reported that fabric softeners increase surface lubricity which results in a corresponding decrease in interfiber friction and an increase in apparent bulk which are responsible for reductions in bending and shear moduli. Changes in yarn bulk also change the contact area with an abradant and the pressure between fibers and yarns at yarn cross-over points. Changes in mechanical properties that are associated with fabric softeners include improvements in resistance to flexural abrasion, pilling, and tearing. Decreases in breaking strength and flat and tumble abrasion resistance also have been attributed to the lubricating effects of softeners. Fabric softeners are of particular interest in the study of fiber transfer and persistence because these finishes are commonly added by consumers during home laundering.

Environmental Factors

Electrostatic properties of fibrous materials and factors that influence charge generation and dissipation on textiles have frequently been discussed as affecting fiber transfer and wear performance of fabrics. The most important factor in determining electrostatic propensity is electrical resistivity which, in turn, is influenced by moisture regain and electrostatic potential of fibers. Similarly, the influence of yarn, fabric and finish structure on electrostatic properties must be considered. Since abrasion and pilling properties are influenced by static electricity, one would expect fiber transfer to be influenced by these variables also. However, Pounds and Smalldon in the study mentioned above have shown that the primary mechanisms of fiber transfer are mechanical rather than electrostatic. One explanation for this may be that fiber transfer usually is a phenomenon that occurs from relatively small stresses that are applied slowly, whereas machines that simulate pilling and abrasion operate at considerably higher levels and rates of stress. The isoelectric values and fabric decay times associated with these processes may therefore be important factors.

Summary

Fiber transfer and the mechanisms that govern this phenomenon have been studied using a variety of different methodologies. Fiber collection studies have been used to evaluate the frequency of occurrence and evidential significance of fibers recovered from clothing and textile materials involved in crimes of violence. These studies have resulted in the development of a data base which currently is used to assess the significance of fibers recovered during criminal investigations.

Surface contact experiments have identified factors that influence fiber transfer from apparel, upholstery, and carpeting. In addition, these studies have used a variety of techniques to induce and evaluate fiber transfer during simulated contact and wear. However, these studies are limited in scope from the standpoint that relatively little attention is given to the influence of fiber properties, yarn structure, and fabric geometry on fiber transfer.

Fiber transfer occurs in response to mechanical stresses encountered during normal use and care of textile materials. An examination of the wear-related properties of textiles (i.e., abrasion, pilling and snag resistance) and the structural characteristics and mechanisms that influence these phenomena can contribute to an understanding of the fiber transfer process. In addition, the influence of fiber, yarn, fabric, and finish parameters on the wear performance properties of textiles can provide insight into the relationship between fiber transfer and the structural characteristics of a textile. Environmental factors can also affect the wear performance properties of fabrics.

While U.S. Pat. No. 4,936,135 to Annis, et al. discloses devices and techniques for evaluating wear properties of materials, greater precision, control and measurement of the numerous variables associated with wear performance properties is desirable. For example, it is desirable to determine precisely the amount of tension on a fabric sample that will be abraded and to measure the amount of abrasion load placed upon the sample. Additionally, the wear tester should be easy to operate, safe and aesthetically attractive.

Moreover, the direction of abrasion (e.g., random or unidirectional) influences material wear, especially for fabrics that have more strength in the warp direction than in the filler direction (or vice versa). Thus, it is desirable to control precisely the relation of the sample material to the abrading material as they are moved relative to one another. Specifically, it is desirable to abrade the material at a constant angle to the warp and filler threads of the material, since this isolates and controls another potentially critical material wear variable. Although U.S. Pat. No. 4,936,135 to Annis, et al. prevents an orbiting pad with an abrasive material from rotating about its central axis, as seen in FIG. 7 the angular relation between warp and filler threads of the sample and abrasive material still changes.

SUMMARY OF THE INVENTION

The present invention provides techniques and devices for evaluating wear properties of materials with greater precision and control, including instrumentation for measuring precisely the variables associated with fabric wear testing. Additionally, the devices provided limit the number of variables that otherwise would affect the results of the fabric wear testing procedure.

According to one device of the present invention, a bottom first pad is stationary and supports a first sample of material (or abradant) and a top second pad rotates or reciprocates with respect to the bottom pad. The relatively large size of the pads more accurately simulate an actual abrasion event to improve the material evaluation. A tension hoop clamps the material between itself and the outer rim of a platform in which the bottom or top pad is held. The platform allows the pad to be raised or lowered, thereby stretching the fabric between itself and the tension hoop to change the tension of the sample material. Strain gauges may be placed on the sample material to measure precisely the amount of tension, which measurement may then be displayed on a control panel.

The combination of the tensioning system (i.e, tension hoop and platform) and measuring system (i.e., strain gauges and control panel) allows a known tension to be uniformly and reproducibly applied to a material sample. The combination also allows the elasticity associated with different materials to be measured and a stretch ratio derived.

The top pad, optionally provided with the tensioning and measuring system, supports a sample of material or abradant. Weights can be attached to the top pad for increasing the load on the bottom pad. Additionally, counterweights are threaded onto a rod attached to the top pad; moving the counterweights along the rod changes the load applied by the top pad to the bottom pad. Such load affects the surface wear of the fabric and accordingly, in one embodiment, a load cell underneath the bottom pad is provided to measure the load. The measurement may then be displayed on a digital readout located on the control panel.

A motor connected to a slide and track translation means allows the top pad to orbit, or by merely repositioning two tabs, reciprocate with respect to the bottom pad. The translation means resolves the rotary forces produced by the motor into two forces, a longitudinal and a transverse force, which are then harnessed by a transmission means to provide orbital or reciprocal motion of the top pad depending on the setting of the translation means. Because of the unique translation means, the orientation of the top pad with respect to the bottom pad is constant during orbital movement. Assuming, for instance, that the top pad is first oriented so that the warp and filling fibers of the material attached to it are parallel to the warp and filling fibers of the material attached to the bottom pad, the translation means maintains that parallel orientation as the top pad orbits. A locator disc with holes drilled at 5° increments around its perimeter may be provided for receiving the bottom first pad. Thus, angle of attack between the test specimen and the fabric abradant can be changed from 0° to 360° (at 5° increments) by altering the position of the bottom pad in the locator disc. Since surface wear is influenced by the direction of abrasion, this embodiment of the invention allows the user to control yet another testing variable.

If desirable, a multiple sample material evaluator, with a plurality of top and bottom pads, can be provided to increase sample throughput. Additionally, a computer can be provided with image analysis software and linked with a video camera to observe and analyze material wear caused by the present invention. The computer also could be interfaced with the material evaluator to store and organize parameters of each test run.

It is accordingly an object of the present invention to provide devices and processes for analyzing fiber transfer and wear properties of materials using various instrumentation to monitor and control closely numerous variables associated with fabric wear testing.

It is an additional object of the present invention to fix the orientation of two materials relative to one other, whether moved in orbital or reciprocating fashion.

It is an additional object of the present invention to provide devices for improving the safety, ease of maintenance and general aesthetic appearance of a materials evaluator device.

It is an additional object of the present invention to provide devices and processes for inducing fiber transfer inexpensively and highly controllably.

Other objects, features and advantages of the present invention will become apparent with respect to the remainder of this document.

DETAILED DESCRIPTION OF THE DRAWINGS

Figure 1A:
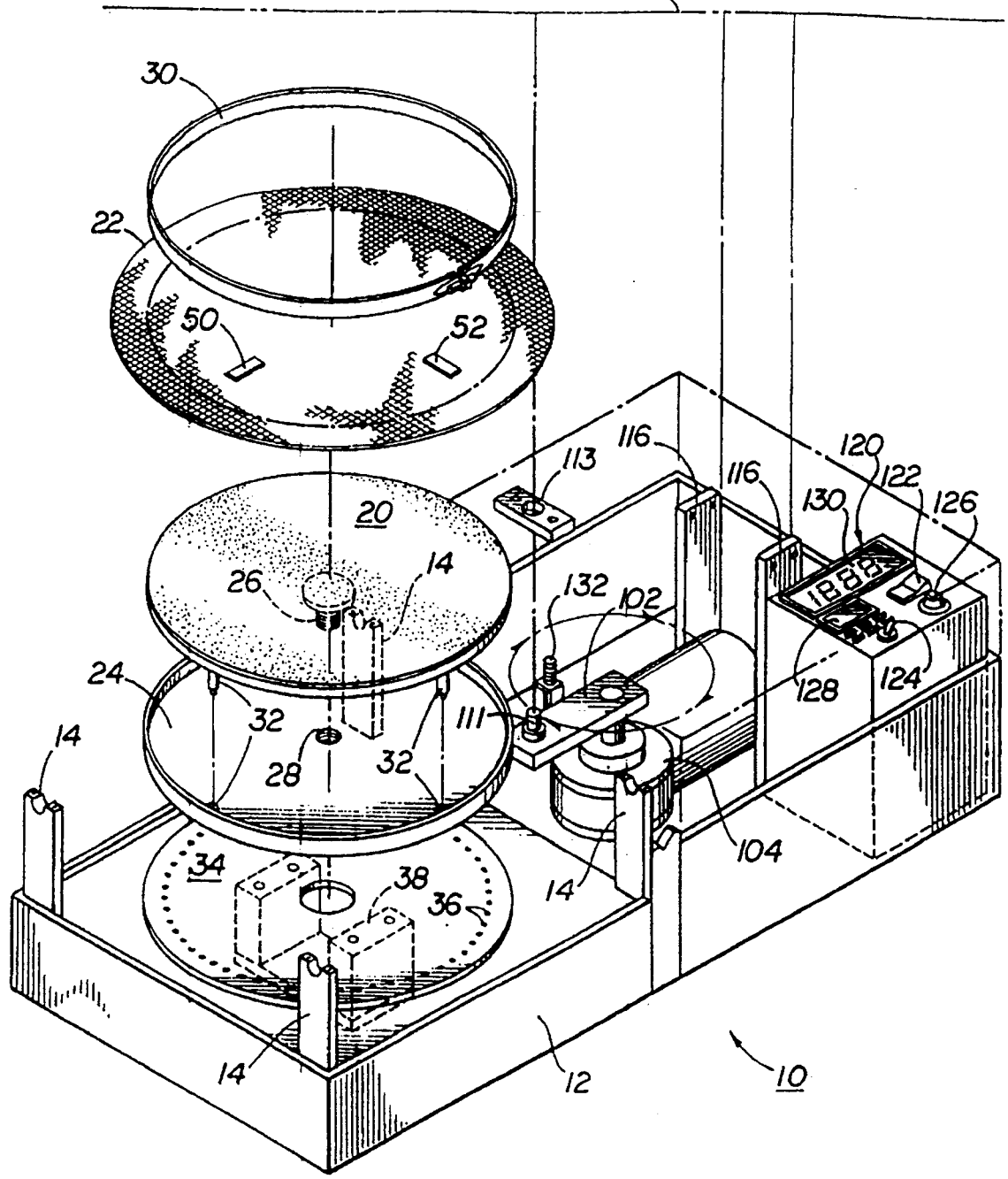
FIGS. 1A and 1B are separated by a match line and together constitute an exploded perspective and cutaway view of a device according to the present invention.
Figure 1B:
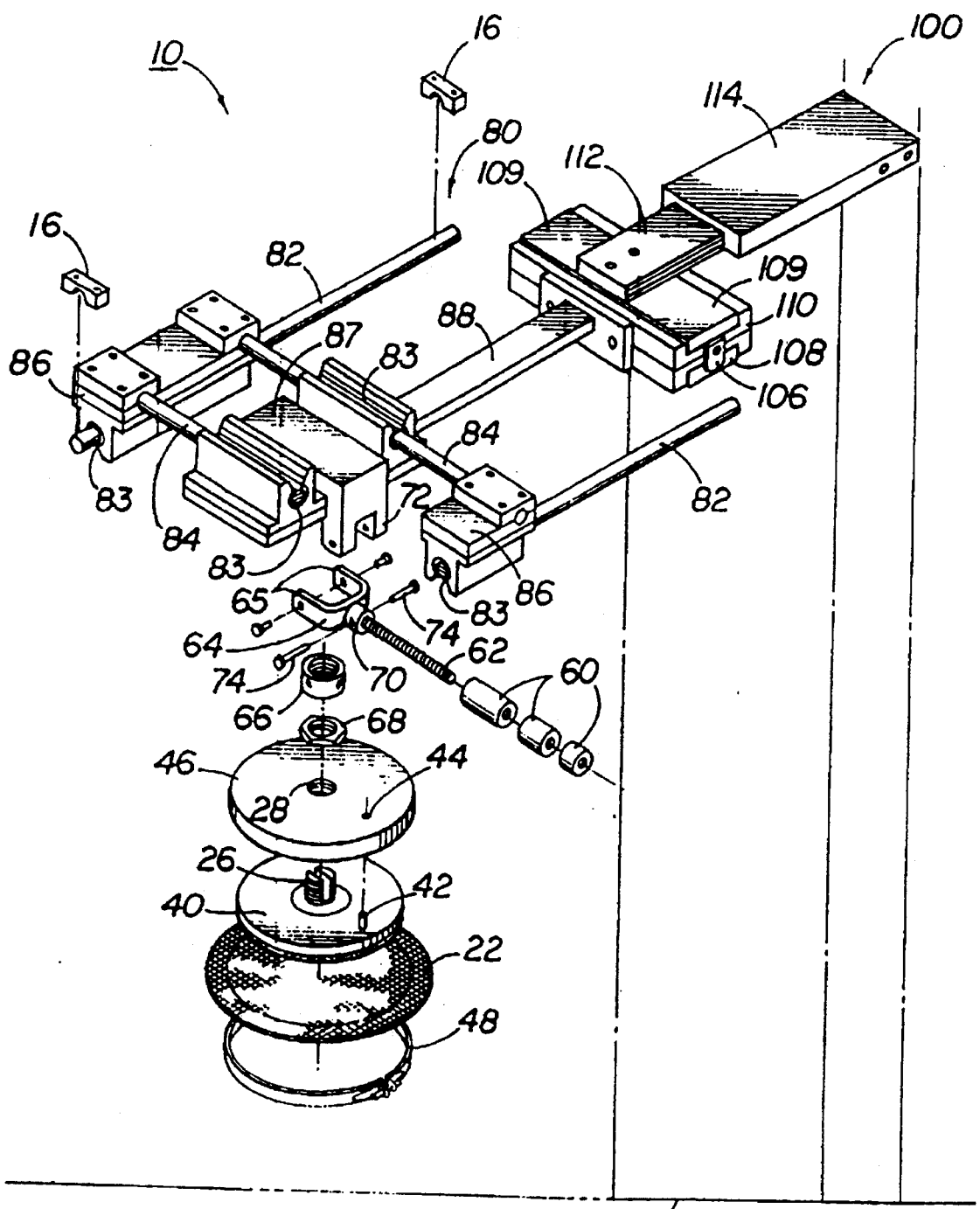

FIGS. 1A–1B show a device 10 for inducing fiber transfer according to the present invention. Device 10 generally comprises a housing 12 that may be formed of square or rectangular tubing and sheet metal or other desirable material. A central bracket divides the housing 12 and supports hinged covers (not shown) that could be formed of a clear plexiglass, so as to allow observation of the abrasion process, or other material. Within the housing 12 is a top first pad 20, a bottom second pad 40 and a drive means, such as a motor 104. Connecting the motor 104 with the second pad 40 is a transmission means 80 that allows motor 104, after its rotary motion has been converted into orbital or reciprocal motion by translation means 100, to move first pad 20 and second pad 40 relative to one another.

First pad 20 and second pad 40 may support specimens of material to be tested for fiber transfer, or abrasive material. FIGS. 1A–B show sample material 22 preparatory to mounting on both first pad 20 and second pad 40. Abrasive material could be mounted on one of the pads, however, and material for testing on the other. The pads 20 and 40, which may be formed of a plastic or metallic material, can be modified to hold carpet, emery paper, cardboard, concrete, foam, plastic or any other test or abrasive material. A common use is to place a donor fabric, for instance, on second pad 40 and a recipient fabric on first pad 20. Generally, such fabric-to-fabric wear simulates well the mechanical forces associated with actual wear conditions. Both first pad 20 and second pad 40 thread on and secure to first platform 24 and second platform 46, respectively, which are each equipped with a jack screw 26 that threads into a bore 28.

A first tension hoop 30 and a second tension hoop 48 secure the material 22 to the appropriate pad. For example, the material 22 is secured to the first pad 20 by placing the first tension hoop 30 so that a portion of the material 22 is caught between the first tension hoop 30 and the edge of the first platform 24. First tension hoop 30 is tightened and then the first pad 20 is raised or lowered upon the jack screw 26 within the first platform 24. Each jack screw 26 has a slot on the end into which a lever can be placed to turn the jack screw 26 and thereby move first pad 20 above the edge of first platform 24. Thus, uniform, peripheral tension on material 22 to stretch it across the surface of first pad 20 is applied. A torque arm and spring scale may be attached to the lever to measure the strain placed on the material 22. Alternatively, strain gauges 50 and 52 measure the strain placed on the fabric in the respective "x" and "y" directions, as shown, or in any other direction. Where the "x" and "y" measurements correspond to the warp and filling threads, the user can, among other things, not only determine the tension applied to a particular material but also can calculate stretch ratios for that material.

While strain gauges 50 and 52 may measure precisely the amount of tension applied to the material 22, a more general indexing pin 42 may also be provided for both the first pad 20 (not shown) and the second pad 40. Indexing pin 42 slides within the bore 44, thereby indicating to the user the relative position of the second pad 40 with respect to the second platform 46. Generally, the farther the indexing pin 42 is recessed into the bore 44, the greater the separation between second pad 40 and second platform 46. As the separation increases, so does the amount of tension or load on the material 22. For particular types of material 22, it may be desirable to calibrate the indexing pin 42 so that a set depth corresponds to a certain amount of tension.

Respecting the first pad 20, locator pins 32 are provided so that first pad 20 can be properly oriented in a locator disc 34. About the perimeter of the locator disc 34 are drilled holes 36 into which locator pins 32 will slide and mate. First pad 20 may be oriented from 0° through 360° in 5° increments, simply by moving the locator pins 32 to appropriate holes 36. Such capability allows the user to control the alignment of the warp and filler threads of a material 22 with respect to an abrading (or another sample) material.

Once placed into locator disc 34, the first pad 20 is directly over load cells 38, which measure the amount of load (or pressure) placed upon the first pad 20 by the second pad 40. That load, normally consisting at least partially of the weight of second pad 40, material 22 and second tension hoop 48, can be increased by attaching ring weights (not shown) to second pad 40. It has been found, however, that light loads closely simulate actual wear conditions. Accordingly, the load may be decreased (to as low as approximately 600 grams in one embodiment) by adjusting several counterweights 60 attached to the second pad 40. Precise fine tuning of the load is possible by reading a digital readout coupled to the load cells 38 while the counterweights 60 are adjusted upon threaded rod 62 that holds the counterweights 60 and is attached to second pad 40 by a mounting yoke 64.

Arms 65 of mounting yoke 64 attach to a mounting collar 66 that abuts against a set nut 68, both of which thread onto the jack screw 26. Mounting yoke 64 also connects with the transmission means 80 via a yoke nut 70 (threaded for adjustment to a desired position along rod 62) that attaches to a yoke bracket 72. Pins 74 hold together yoke nut 70 and yoke bracket 72. The second pad 40 is thereby coupled with the transmission means 80.

Transmission means 80 has two longitudinal slide rods 82 (corresponding to the "x" direction) and two transverse slide rods 84 (corresponding to the "y" direction). Longitudinal slide rods 82 are held to columns 14 of housing 12 via caps 16 and support a pair of carriage plates 86. Linear bearings 83 allow carriage plates 86 to slide along longitudinal slide rods 82. Connecting to the top of carriage plates 86 are the ends of transverse slide rods 84. Suspended from transverse slide rods 84, via linear bearings 83, is an assembly 87, which generally connects transmission means 80, via yoke bracket 72, with second pad 40. Bar 88 attaches both to assembly 87 and translation means 100, which translates the rotary motion of crank 102 driven by motor 104 into either orbital or reciprocating motion. See FIG. 1A. During orbital motion, assembly 87 slides along transverse slide rods 84 and carriage plates 86 slide along longitudinal slide rods 82. When reciprocal motion is chosen, assembly 87 is centered, as shown in FIG. 1B, and does not move along transverse slide rods 84. Reciprocal motion occurs as carriage plates 86 slide along longitudinal slide rods 82, thereby causing transverse slide rods to move and carry assembly 87 through the center of first pad 20.

Such orbital or reciprocal motion is made possible by the transmission means 80 working in concert via bar 88 with translation means 100, which converts the rotary motion of crank 102 as it is turned by motor 104 into either orbital or reciprocal motion. Basically, translation means 100 resolves the rotary motion into vector forces acting in only two directions, the longitudinal or "x" direction and the transverse or "y" direction. Rotary motion is communicated by post 111 of crank 102 that slides into, and rotates within, anchor bracket 113 that is firmly fixed to a bottom slide 108. Orbital motion is achieved by setting two tabs 106 (one of which is not shown) in the "down" position, as seen in FIG. 1B. This prevents bottom slide 108 from moving within a transverse track 110 to the center of which is affixed one end of bar 88. Thus, as crank 102 turns, bottom slide 108 remains fixed within transverse track 110. Transverse force produced by turning of crank 102 causes transverse track 110 to move along top slide 109. Additionally, force produced from the rotation of crank 102 causes longitudinal slide 112, which is connected to top slide 109, to move within a longitudinal track 114. The longitudinal track 114 is fixed to a bracket 116 and is perpendicular to transverse track 110.

Figure 3:
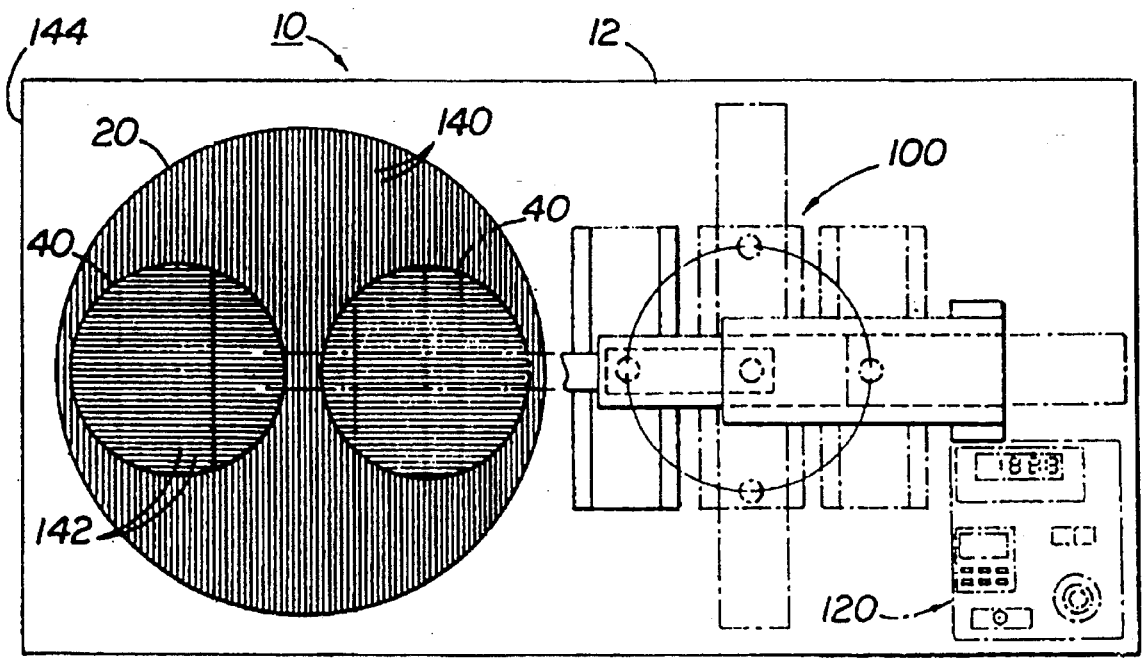
FIG. 3 is a schematic view of the device of FIG. 1 set for abrading material samples in reciprocating fashion.

Setting tabs 106 in the "up" position, which is possible when assembly 87 is centered over first pad 20, as shown in FIG. 3, selects reciprocal motion. When tabs 106 are set in the "up" position, transverse track 110 no longer will be able to move along top slide 109. Both top slide 109 and transverse track 112 are thereby in fixed perpendicular relationship with longitudinal track 114. Bottom slide 108 may still move in the now fixed transverse track 114, and by so doing, expend the transverse forces produced by rotary motion of crank 102. Accordingly, rotation of crank 102 is translated into reciprocating motion of longitudinal slide 112 within longitudinal track 114 that is then communicated through transmission means 80 to second pad 40. Such reciprocation occurs through the center of first pad 20.

Control panel 120 provides means for controlling the speed and number of cycles of motor 104 and provides readouts of the amount of load second pad 40 applies to first pad 20. Using digital displays in the control panel 120 simplifies operation and improves the reproducibility of parameters used in abrading materials. An On/Off switch 122 controls power to the device 10, allowing the user to energize control panel 120 independently of actually moving second pad 40, since a separate stop/start switch 124 controls actuation of motor 104. The speed of motor 104 may be controlled by a potentiometer 126, in combination with a speed chart that displays the rpm (rotations per minute) corresponding to the dial setting of the potentiometer 126. A microprocessor 128 displays the number of cycles of reciprocation or orbital movement (up to six digits) and is programmable for single or multiple cycle test runs. At the end of each programmed test run, the second pad 40 returns exactly to its start point on the first pad 20. Each cycle of movement is detected by a sensor 132 that couples to the microprocessor 128. Sensor 132 may be a magnetic, photoelectric or other well known sensing device. Similarly, the display 130 is coupled to load cells 38, thereby to display (in grams or other desired units) the load that second pad 40 places upon first pad 20.

Figure 2:
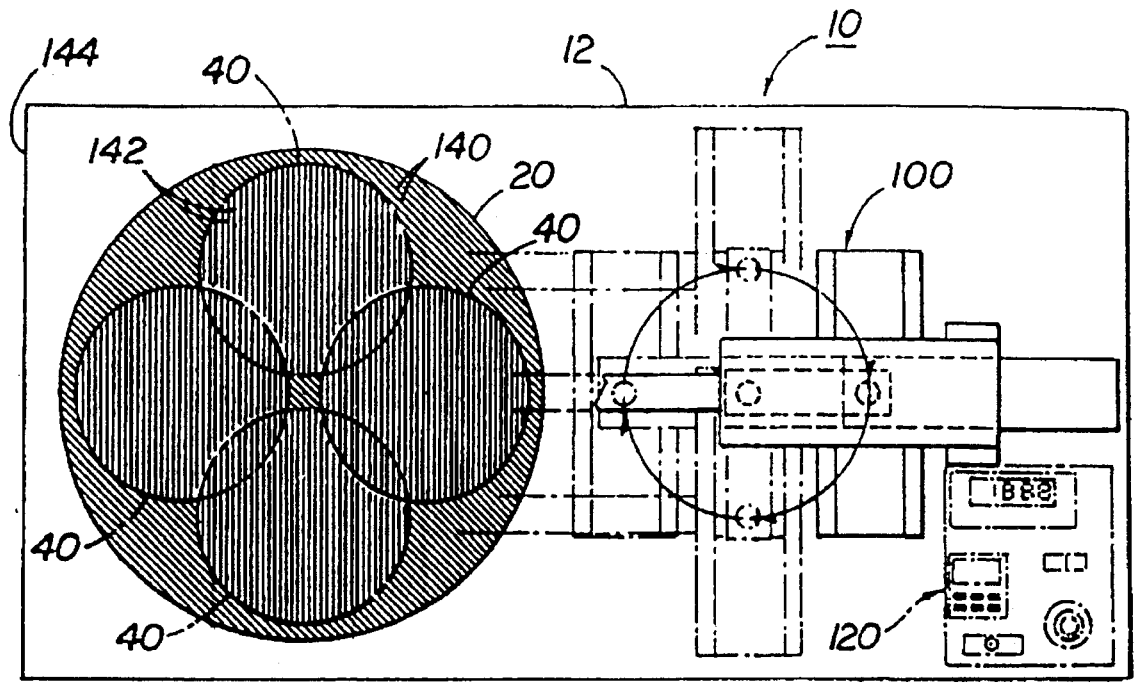
FIG. 2 is a schematic view of the device of FIG. 1 set for abrading material samples in orbital fashion.

FIGS. 2 and 3 depict schematically device 10 in actual use. FIG. 2 shows device 10 with translation means 100 set to provide orbital motion of second pad 40 over first pad 20. As it orbits, control panel 120 monitors the load applied by second pad 40 on first pad 20, as well as the number of cycles of orbit. First pad 20 is arranged within locator disc 34 so that warp threads 140 of some material held by first pad 20 are at approximately a forty five degree (45°) angle to warp threads 142 (that are parallel with edge 144 of device 10) of the material held on second pad 40. As is clear from FIG. 2, as second pad 40 orbits about first pad 20, the warp threads 140, 142 maintain their angular relationship. Obviously, the filler threads (not shown) of the material on first pad 20 would also maintain constant angular relationship with corresponding filler threads on second pad 40. Controlling such angular relationship may be critical since alignment of fabrics during abrasion influences the type and severity of surface wear. Moreover, maintaining constant angular relationship also means that at any speed of motor 104 the velocity of second pad 40 as it travels across first pad 20 remains constant so that abrasion is uniformly applied across the entire surface of first pad 20.

FIG. 3 depicts device 10 with translation means 100 set for reciprocating motion. Warp threads 140 of the material held by first pad 20 are made parallel with edge 144 by locating first pad 20 within the appropriate holes 36 of locator disc 34. Warp threads 142 of the material held by second pad 40 are perpendicular to both the warp threads 140 and edge 144. Changing the location of first pad 20 within locator disc 34 sets the angular relationship between the materials.

The entire device 10 may be encased in a black plexiglass frame. A clear plexiglass lid allows an unobstructed view of the test material during operation. If desirable, a video camera can observe the test material through the clear plexiglass and be interfaced with a personal computer. Image analysis software on the personal computer may allow measurements, for example, of pilling frequency, size, size distribution and pill density to be obtained and stored automatically. Additionally, the control panel 120 can be interfaced with the personal computer so that parameters associated with each test run are stored with quantitative results. A safety switch prevents operation of device 10 when the lid is open, thus providing protection from moving parts. Finally, device 10 may be easily maintained, requiring only lubrication of the transverse and longitudinal slides depending upon amount of use.

The foregoing is provided for purposes of illustration and explanation. Modifications may be made to the device and processes described above without departing from the scope or spirit of the invention.

What is claimed is:

1. A device for testing wear properties of materials, comprising:
   (a) a first pad and a second pad, each with a surface for receiving materials and designed to move relative to one another;
   (b) a first tensioning means, coupled to the first pad, for uniformly applying tension to received material;
   (c) a second tensioning means, coupled to the second pad, for uniformly applying tension to received material; and
   (d) drive means, attached to the first pad, for causing the first pad to orbit about the second pad without angulation.

2. A device according to claim 1 further comprising means for measuring the tension of the received material.

3. A device according to claim 2 further comprising means for adjusting the pressure between the first pad and the second pad.

4. A device according to claim 3 further comprising a load cell for measuring the pressure between the first pad and the second pad.

5. A device according to claim 4 further comprising a control panel for displaying the tension measurement and the pressure measurement.

6. A device for testing wear properties of materials, comprising:
   (a) a housing;
   (b) a first pad secured to a platform for receiving a first material, comprising:
      (i) means for fixing the first material to the first pad; and
      (ii) means for changing the tension of the first material by moving the first pad in relation to the platform;
   (c) a locator disc, with an outer perimeter in which apertures are formed, for receiving the first pad;
   (d) a second pad for receiving a second material;
   (e) means for causing moving contact between the first pad and the second pad, comprising:
      (i) drive means for rotating a shaft;
      (ii) translation means for translating the rotation of the shaft to reciprocating or orbital motion; and
      (iii) transmission means for transmitting the reciprocating or orbital motion produced by the translation means to cause movement between the first pad and second pad so that the first material is held in a constant angular relationship with the second material; and
   (f) means for varying the pressure between the first pad and the second pad.

7. A device according to claim 6 further comprising a control panel, having:
   (a) a switch for actuating the drive means;
   (b) a microprocessor, coupled to a sensor, for controlling and displaying the number of cycles of reciprocating or orbital movement.

8. Apparatus for testing wear properties of materials while controlling and measuring certain of the variables associated with testing material wear, comprising:
   (a) a housing;
   (b) a first pad and a second pad, each with a surface for receiving materials and designed to move relative to one another;
   (c) a motor, cooperating with a control means, for controlling the speed and number of cycles made by the motor;
   (d) translation means, connecting to the motor, for translating the force produced by the motor into orbital or reciprocal motion;
   (e) a transmission, connecting to the second pad and the translation means, comprising:
      (i) at least two longitudinal rods;
      (ii) at least two transverse rods;
      (iii) means for connecting the longitudinal rods with the transverse rods; and
      (iv) means for attaching to the second pad.

9. Apparatus according to claim 8 further comprising means for adjusting the pressure between the first pad and the second pad.

10. Apparatus according to claim 9 wherein the control means further comprises a display coupling to a sensor that determines the pressure between the first pad and the second pad.

11. Apparatus according to claim 8 further comprising means for adjusting the tension of the material received by the first pad or the second pad.

12. Apparatus according to claim 11 wherein the control means further comprises means for reading the tension of the material received by the first pad or the second pad.

13. Apparatus according to claim 8 further comprising means for adjusting the angular relationship of the first pad relative to the second pad.

14. Apparatus according to claim 8 wherein the translating means comprises:
   (a) at least two transverse slides, both of which are held in a first track;
   (b) a longitudinal slide, connected to at least one of the transverse slides, held in a second track; and
   (c) means for restraining at least one of the transverse slides so that it does not move within its track.

15. A device for causing material wear by abrading material and evaluating the abrading process, the device comprising:
   (a) a motor attached to translation means for translating motion produced by the motor into orbital or reciprocal motion, the translation means comprising:
      (i) a plurality of transverse slides located within a first track, at least one of which is connected to and driven by the motor;
      (ii) a longitudinal slide located within a second track; and
      (iii) tabs for restraining at least one of the transverse slides within the first track to cause either orbital or reciprocal motion;
   (b) transmission means, attached to the translation means and to a first means for holding a material, for transmitting the orbital or reciprocating motion of the translation means to the first holding means;
   (c) second means for holding a material positioned so that the first holding means will be caused by the transmission means to move over the second holding means; and
   (d) a control panel.

16. Apparatus according to claim 15 wherein the first holding means comprises a pad to which weights can be attached to increase the pressure of the pad upon the second holding means.

17. Apparatus according to claim 16 wherein the control panel comprises:
   (a) means for controlling the speed of the motor;
   (b) means for programming the number of cycles of the motor; and
   (c) means for displaying the amount of pressure between the first holding means and the second holding means.

18. A device for causing and evaluating material wear, comprising:
   (a) holding means for receiving and holding a first material;
   (b) drive means for producing rotary motion;
   (c) a slide and track system, connecting to the drive means, for creating orbital or reciprocal motion, comprising:
      (i) a first transverse slide held within a first track;
      (ii) a second transverse slide held within a second track; and
      (iii) a longitudinal slide held within a third track;
   (d) means for transmitting the orbital or reciprocal motion to the holding means thereby to move it over a surface and cause abrasion, comprising:
      (i) at least two longitudinal rods;
      (ii) at least two transverse rods;
      (iii) means for connecting the longitudinal rods with the transverse rods; and
      (iv) means for attaching to the holding means.

* * * * *